United States Patent
Budowsky et al.

[11] Patent Number: 5,955,446
[45] Date of Patent: Sep. 21, 1999

[54] METHOD OF TREATING HERPES INFECTIONS WITH 2',5'-OLIGOADENYLATE-2',3'-CYCLOPHOSPHATE COMPOUNDS

[75] Inventors: Edward I. Budowsky, Brookline; Samuel K. Ackerman, Weston, both of Mass.

[73] Assignee: Pentose Pharmaceuticals, Inc., Cambridge, Mass.

[21] Appl. No.: 08/784,801

[22] Filed: Jan. 16, 1997

[51] Int. Cl.$^6$ .............................. A01N 43/04; C07H 21/02
[52] U.S. Cl. ............................. 514/47; 536/25.2
[58] Field of Search ................................ 514/43, 44, 45, 514/46, 47; 536/22.1, 25.2

[56] References Cited

U.S. PATENT DOCUMENTS

| | | | |
|---|---|---|---|
| 4,464,359 | 8/1984 | Suhadolnik et al. | 514/47 |
| 4,476,301 | 10/1984 | Imbach et al. | 536/25.2 |
| 4,515,781 | 5/1985 | Torrence et al. | 514/44 |
| 4,539,313 | 9/1985 | Suhadolnik et al. | 514/47 |
| 4,708,935 | 11/1987 | Suhadolnik et al. | 435/91.5 |
| 4,859,768 | 8/1989 | Suhadolnik et al. | 536/25.2 |
| 4,924,624 | 5/1990 | Suhadolnik et al. | 47/58 |
| 4,981,957 | 1/1991 | Lebleu et al. | 536/25.2 |
| 4,990,498 | 2/1991 | Suhadolnik | 514/47 |
| 5,188,897 | 2/1993 | Suhadolnik et al. | 428/402.2 |
| 5,405,939 | 4/1995 | Suhadolnik et al. | 530/322 |
| 5,739,013 | 4/1998 | Budowsky et al. | 435/91.1 |

FOREIGN PATENT DOCUMENTS

| | | |
|---|---|---|
| 4211237A1 | 10/1993 | Germany . |
| 4211238C2 | 10/1994 | Germany . |
| 36176527 | 8/1986 | Japan . |
| 9221691 | 12/1992 | WIPO . |

OTHER PUBLICATIONS

Liu et al. "Mechanism of Interferon Action III–Significace of pppA2'p5'A2'p5'A in the Antiviral Action of Interferon," *Scientia Sinica* (Series B) (1983) 26: 8: 809–815, 1983.

Goswami et al. "Mechanism of Inhibition of Herpesvirus Growth by 2',5'–Linked Trimer of 9–beta–D–Xylofuranosyladenine," *Virology* (1984) 137: 400–407, 1984.

Eppstein et al. "Xyloadenosine Analog of (A2'p)2–A Inhibits Replication of Herpes Simplex Viruses 1 and 2," *Nature* (1983) 302: 723–724, 1983.

Fujihara et al. "Effect of 2',5'–oligoadenylate on Herpes simplex virus–infected cells and preventive action of 2',5'–oligoadenylate on the lethal effects of HSV–2," *J. Interferon Res.* (1989) 9:691–707.

S. Shigeta et al., "Preparation of peptide conjugates with 2',5'–oligoadenylates as antitumor and antiviral agents," *Chemical Abstracts* 113:152984p (1990).

Doetsch et al.; "Core (2'–5')oligoadenylate and the cordycepin analog; Inhibitors of Epstein–Barr virus–induced transformation of human lymphocytes in the absence of interferon"; *Proc. Natl. Acad. Sci. USA*, 78(11):6699–6703 (1981).

Black et al.; "2',5'–Oligoadenylate Trimer Core and the Cordycepin Analog Augment the Tumorcidal Activity of Human Natural Killer Cells"; *J. of Immunology*, 135(5):2773–2777 (1984).

Henderson et al.; "Inhibition of Epstein–Barr Virus–Associated Nuclear Antigen (EBNA) Induction by (2',5')Oligoadenylate and the Cordycepin Analog: Mechanism of Action for Inhibition of EBV–Induced Transformation"; *Virology*, pp. 198–201 (1982), vol. 122.

Torrence et al.; "Methods for the Synthesis of Analogs of (2'–5')–Oligoadenylic Acid"; *Methods in Enzymology*, 119:522–529 (1986).

Devash et al.; "Measurement of Effect (2'–5')–Oligoadenylates and Analogs on Tobacco Mosaic Virus Replication"; *Methods in Enzymology*, 119:759–761 (1986).

Johnston et al.; "The Role of Interferon–induced proteins, double–stranded RNA and 2',5'–oligoadenylate in the interferon–mediated inhibition of viral translation"; *Interferon*, 3(7):201–298 (1984).

Suhadolnik et al.; "Measurement of Effect of (2'–5')–Oligoadenylates and Analogs on Protein Synthesis and Growth of Cells"; *Methods in Enzymology*, 119:667–675 (1986).

Nolan–Sorden et al.; "Photochemical Crosslinking in Oligonucleotide–Protein Complexes between a Bromine–Substituted 2–5A Analog and 2–5A–Dependent RNase by Ultraviolet Lamp or Laser"; *Analytical Biochemistry*, 184:298–304 (1990).

Itkes et al.; "A route to 2',5'–oligoadenylates with increased stability towards phosphodiesterases"; *Febs Letters*, 236(2):325–328 (1988).

*Primary Examiner*—Jon P. Weber
*Assistant Examiner*—Susan Hanley
*Attorney, Agent, or Firm*—Myers Bigel Sibley & Sajovec

[57] ABSTRACT

The present invention provides methods for treating herpes infections in a subject in need of such treatment, by the administration of 2'–5' oligoadenylate-2',3'-cyclophosphate compounds. Pharmaceutical formulations comprising 2'–5' oligoadenylate-2',3'-cyclophosphate and compounds thereof are also provided.

6 Claims, No Drawings

METHOD OF TREATING HERPES INFECTIONS WITH 2',5'-OLIGOADENYLATE-2',3'-CYCLOPHOSPHATE COMPOUNDS

FIELD OF THE INVENTION

The present invention relates generally to a method of treating viral infections, and more specifically to a method of treating herpes infections.

BACKGROUND OF THE INVENTION

Herpes simplex virus (herpes simplex virus type 1, or HSV-1, and herpes simplex virus type 2, or HSV-2) produce a variety of infections involving vesicular eruptions on the skin and mucus membranes, and may also affect the central nervous system and occasionally visceral organs. HSV-1 is associated mainly with the oral region (oral herpes) and causes cold sores and fever blisters. HSV-2 causes lesions that are similar to oral herpes, but that occur mainly in the genital region (genital herpes). Herpes viruses are particularly deleterious pathogens because of their potential for persistence in cells, their transformation of normal cells into cells showing uncontrollable proliferation, and their affinity for nerve tissue. Once herpes viruses have infected, they may persist in the host cells. For example, after infecting epithelial cells, herpes simplex viruses secondarily invade nerve tissues and remain latent in them. With HSV-1, latency occurs in facial nerve tissue (the trigeminal ganglion). HSV-2 establishes latency in the sacral ganglia, which are in the pelvic region. P. J. VanDemark and B. L. Batzing, *The Microbes* (1987).

Most people have been infected with HSV-1 by the time they reach adulthood; about half of children between one and five years old have been infected. As a consequence of latency, herpes viruses may appear periodically to cause recurrent disease. Recurrence is common, and may be stimulated by various physiological stresses, trauma, emotional stress, and hormonal changes.

HSV-2 is a particularly important public health problem. First, it is a sexually transmitted disease for which there is no cure. In 1987, the annual incidence of HSV-2 infection in the United States alone was estimated to be in the range of 200,000–500,000 cases. Depending on the level of sexual activity and socioeconomic factors, the overall prevalence of HSV-2 virus in the population has been estimated to be within 10% and 70%. Additionally, if HSV-2 infection is transmitted to newborns during birth, the subsequent infection may be devastating. It has been estimated that at least 50% of newborns delivered by women with genital herpes become infected with HSV-2; about half of these infants suffer severe virus-induced defects, such as retardation.

Thirdly, there are numerous associations between herpes virus infections and the contracting or development of other serious diseases. For example, there is an established link between HSV-2 infection and cervical cancer. Herpes virus has been shown to transform normal cells into cancer cells under laboratory conditions. HSV-2 infection has also been found to be a risk factor for the acquisition and transmission of infection of HIV-1, the virus thought to be the cause of AIDS. HSV-1 is also associated with the incident of other diseases, such as viral encephalitis.

Several methods have been proposed and used as treatments for herpes infection, including the administration of various pharmaceuticals, such as iododeoxyuridine, adenine arabinoside (ara-A) and acycloguanosine (acyclovir). Iododeoxyuridine and ara-A are used to treat HSV-1 eye infections, while ara-A may reduce the severity of encephalitis caused by HSV-1 and HSV-2 infection of newborns. Acyclovir is currently considered to be the mainstay of drug therapy in the treatment of herpes, both genital and oral. However, none of these methods has proved to be entirely effective. For example, while acyclovir has been shown to speed the healing and resolution of genital herpes infections, the benefit of treating acute episodes of recurrent genital disease is quite modest and not recommended as a long-term therapy. L. Corey, "Herpes Simplex Viruses" in Harrisons' *Principles of Internal Medicine* 13th Edition, K. J. Isselbacher et al., eds., p. 786 (1994). Acyclovir has a very limited benefit with regards to oral herpes; in many cases, developing lesions are not aborted and healing time is not reduced. Most seriously, acyclovir-resistant strains of herpes viruses are being idenitified with increasing frequency, especially in HIV-infected person. There is therefore a desire to develop a method of treating herpes infections that is effective, safe and practical.

SUMMARY OF THE INVENTION

In view of the foregoing, it is a first object of the present invention to provide a method for effectively and practically treating a herpes viral infection.

A second object of the invention is to provide pharmaceutical formulations useful in the treatment of herpes infections.

It has now been discovered that 2'–5' oligoadenylates (2',5'-A) and their analogs are surprisingly effective in the treatment of herpes infections. Accordingly, a first aspect of the present invention is a method of treating a herpes infection in a subject in need of such treatment. The method comprises administering to the subject a compound of Formula I:

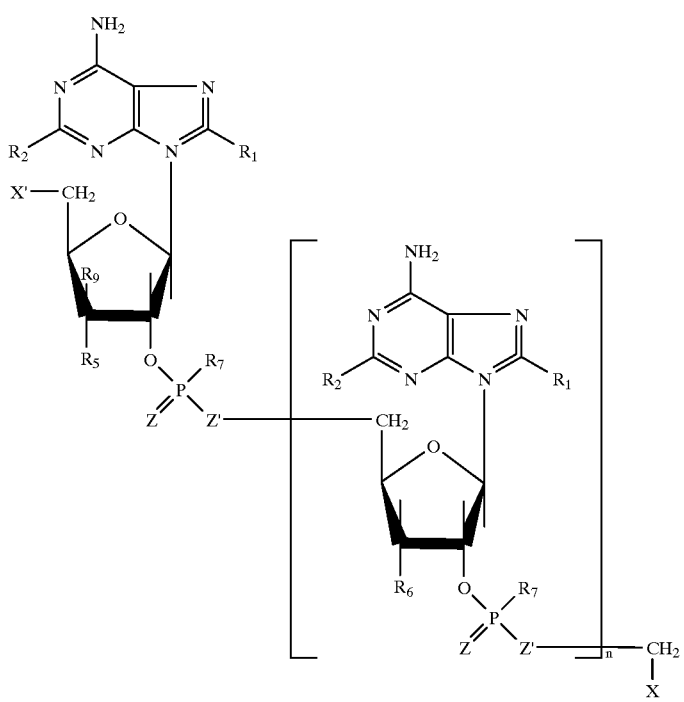

(I)

wherein n is 0, 1, 2, or 3;

each $R_1$ and $R_2$ is independently selected from the group consisting of hydrogen, halogen, and $N_3$;

each $R_5$ is independently hydrogen or —OH;

each $R_6$ is independently hydrogen or —OH;

$R_7$ is $O^-$ or —OH;

$R_9$ is hydrogen or —OH, with the proviso that when $R_9$ is —OH, $R_5$ is hydrogen;

$X_1$ is

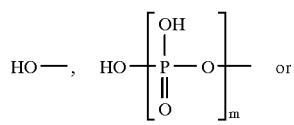 or

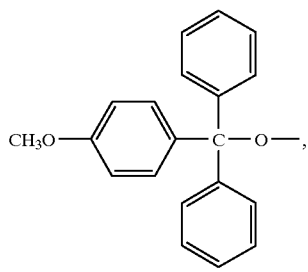

wherein m is 1, 2, or 3;

X is —CHOHCH$_2$OH, or is selected from the group consisting of

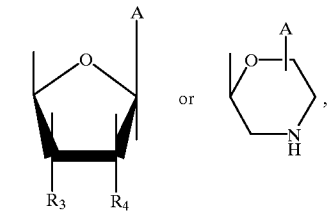

wherein $R_3$ is —OH and and $R_4$ is —PO$_4^{-2}$; or $R_3$ is —PO$_4^{-2}$ and and $R_4$ is —OH; or $R_3$ and $R_4$ together represent a cyclophosphate; and A is selected from the group consisting of:

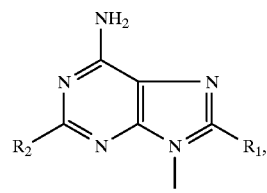

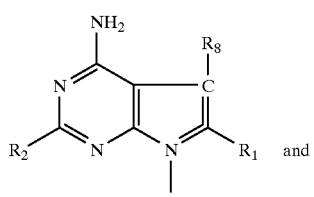 and

-continued

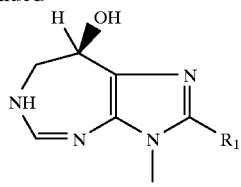

wherein each $R_1$ and $R_2$ are as provided above; and $R_8$ is selected from the group consisting of hydrogen, cyanogen, and amido;

each Z is independently O or S;

and each Z' is independently O or S;

or a pharmaceutically acceptable salt thereof (hereinafter referred to as the "active compound"), in an amount effective to combat the herpes infection.

In one preferred embodiment of the invention, Y is —OH. In another preferred embodiment of the invention, X is

A is

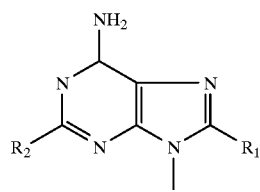

$R_1$ and $R_2$ are hydrogen;
$R_3$ is —OH and $R_4$ is —$PO_4^{-2}$, or
$R_3$ is $PO_4^{-2}$ and $R_4$ is —OH, or
$R_3$ and $R_4$ together represent a cyclophosphate;
$R_5$ is —OH;
$R_0$ is hydrogen; and
Z and Z' are both O.

A second aspect of the present invention is a pharmaceutical formulation for combatting herpes infection comprising, in combination with a pharmaceutically acceptable carrier, an active compound as described above.

A third aspect of the present invention is the use of an active compound as disclosed herein for the manufacture of a medicament useful in carrying out a therapeutic method of treatment as given above.

DETAILED DESCRIPTION OF THE INVENTION

As noted above, the methods of the present invention are useful for treating infections caused by herpes viruses. In general, herpes viral infections (the "condition") are characterized by lesions on the skin and mucus membranes, sometimes accompanied by fever, malaise, irritability and the inability to eat. In oral herpes, lesions may involve the hard and soft palate, gums, tongue, lip and facial area. In genital herpes, the appearance of lesions on the genitals may further be accompanied by pain, itching, vaginal or urethral discharge and dysuria. Lesions may also spread to the rectal and perianal regions. See Corey, supra, at 784. The methods of the present invention are useful for treating these conditions in that they inhibit the onset, growth, or spread of the condition, cause regression of the condition, cure the condition, or otherwise improve the general well-being of a subject afflicted with, or at risk of contracting the condition.

Subjects to be treated by the methods of the present invention are typically human subjects, although the methods of the present invention may be useful with any suitable subject known to those skilled in the art including mammals (e.g., horses, dogs, cats) for veterinary purposes.

As used herein, the term "herpes virus" refers to either the herpes simplex virus-1 (HSV-1) or herpes simplex virus-2 (HSV-2). The herpes virus virion is characterized as containing a linear, double stranded DNA (about $100 \times 10^6$ daltons in molecular weight) that encodes more than 60 gene products. Corey, supra at 782. The genomic structures of the two HSV subtypes are similar, and the sequence homology between HSV-1 and HSV-2 is about 50%. The viral genome is packaged within a regular icosahedral protein shell (capsid). Additionally, the outer covering of the virus is a lipid-containing membrane (envelope) derived from modified cell membrane. Id.

Active compounds of the present invention are, in general, 2'-5' oligoadenylates and their analogs which have anti-herpes activity. In particular, active compounds of the present invention are of Formula I, as set forth above.

In one particularly preferred embodiment of the invention, the $X^1$ group of the above Formula I is —OH. In another particularly preferred embodiment of the invention, X is

A is

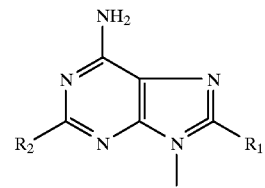

$R_1$ and $R_2$ are hydrogen;
$R_3$ is —OH and $R_4$ is —$PO_4^{-2}$; or
$R_4$ is —OH and $R_3$ is —$PO_4^{-2}$; or
$R_3$ and $R_4$ together represent a cyclophosphate;

$R_5$ is —OH;

$R_0$ is hydrogen; and

Z and Z' are both O.

2'–5' oligoadenylate compounds and their analogs are known. Exemplary compounds include 2'–5' oligoadenylate, the 2',5'-oligoadenylate- 2',3' cyclophosphates disclosed in German Patent DE 42 11 237 A1 to Budowsky, et al.; the 2',5'-oligoadenylate phosphate-containing derivatives disclosed in German Patent DE 42 11 238 C2 to Budowsky et al.; the 2'- and 8-azido(2'–5')oligoadenylates disclosed in U.S. Pat. No. 4,990,498 to Suhadolnik; the 2'–5'-phosphorothioate oligoadenylates in disclosed in U.S. Pat. No. 5,188,897 to Suhadolnik et al.; the 2'–5'riboadenylate-morpholinoadenylate oligonucleotides disclosed in U.S. Pat. No. 4,515,781 to Torrence et al.; the (2'–5')-oligo(3'-deoxyadenylates) and derivatives thereof disclosed in U.S. Pat. No. 4,464,359 to Suhadolnik et al.; the 2'–5'oliogadenylate cordycepin analogs as disclosed in U.S. Pat. No. 4,859,768 to Suhadolnik et al.; the 2'–5' oligoxyloadenylates disclosed in U.S. Pat. No. 4,476,301 to Imbach et al.; and the 8-azaadenosine, sagivamycin, toyocamycin, tubericidine, and 8-bromo-adenosine analogs of 2'–5' oligoadenylates as disclosed in U.S. Pat. No. 4,981,957 to Lebleu et al. (applicants specifically intend that the disclosure of these and all other patent references cited herein be incorporated by reference herein in their entirety).

Specific compounds useful in the practice of the present invention include, but are not limited to, 2',3'-cyclophosphateadenylyl(2',5')adenylyl-(2',5')adenosine (Papirine AIII), 2',3'-cyclophosphateadenylyl(2',5')adenylyl (2',5')adenylyl-(2',5')adenosine (Papirine AIV), 2',3'-cyclophosphateadenylyl(2',5')adenosine (Papirine AII), 2'-phosphateadenylyl(2',5')adenylyl-(2',5')adenosine (Papirine BIII), 3'-phosphateadenylyl(2',5')adenylyl-(2',5') adenosine (Papirine BIII), 2'-phosphateadenylyl(2',5') adenylyl(2',5')adenylyl-(2',5')adenosine (Papirine BIV), 3'-phosphateadenylyl(2',5')adenylyl(2',5')adenylyl(2',5')-adenosine (Papirine BIV), 2'-phosphateadenylyl(2',5') adenosine (Papirine BII), 3'-phosphateadenylyl(2',5') adenosine (Papirine BII), adenylyl(2',5')adenylyl(2',5') adenosine (Papirine CIII), adenylyl(2',5')adenylyl(2',5') adenylyl-(2',5')adenosine (Papirine CIV), adenylyl(2',5')-adenosine (Papirine CII), adenylyl(2',5')adenylyl (2',5') tubercidin and the 5' mono-, di-,and triphosphates thereof, 5'-O-p-methoxytrityladenylyl(2',5')adenylyl(2',5') adenosine, xyloadenylyl(2',5')xyloadenylyl(2',5') xyloadenosine, (Rp)-P-thioadenylyl-(2',5')-(Sp)-thioadenylyl(2',5')adenosine, and (Sp)-P-thioadenylyl-(2',5')-(Rp)-thioadenylyl(2',5')adenosine.

Compounds of the present invention may be prepared using chemical enzymatic synthesis methods which will be apparent to one skilled in the art. For example, 2',5'-oligoadenylate-2'3'-cyclophosphates may be produced beginning with poly(A) with irregular 2',5' and 3',5' internucleotide bonds, using the procedure of Michaelson (A. M. Michaelson, *The Chemistry of the Nucleosides and Nucleotides*, 418–19 (1963)), by the chemical polymerization of 2'(3') adenosine monophosphate. The subsequent split of the 3'5' bonds in this polymer by ribonuclease leads to a monomer and 2,'5 oligoadenylates of varying lengths with a mixture containing a terminal 2',3' cyclophosphate group. By keeping the mixture at a low pH, the terminal cyclophosphate can be opened to provide other compounds useful in the method of this invention. Additional synthetic pathways useful in providing compound useful in the invention are disclosed in U.S. Pat. No. 4,981,957 to Lebleu et al., U.S. Pat. No. 4,708,935 to Suhadolnik et al., U.S. Pat. No. 4,990,498 to Suhadolnik et al., U.S. Pat. No. 4,515,781 to Torrence et al., and U.S. Pat. No. 4,476,301 to Imbach et al.

The active compounds described herein can, as noted above, be prepared in the form of their pharmaceutically acceptable salts. Pharmaceutically acceptable salts are salts that retain the desired biological activity of the parent compound and do not impart undesired toxicological effects. Examples of such salts include salts derived from bases, such as ammonium salts; alkali metal salts such as those of sodium and potassium; alkaline earth metal salts such as those of calcium and magnesium; and salts with organic bases such as triethylamine, dicyclohexylamine, and the like.

In order to enhance the intracellular transport of the active compounds, the compounds can also be conjugated to macromolecular carriers (e.g., poly(L-lysine)), as described in U.S. Pat. No. 5,405,939 to Suhadolnik et al.

The therapeutically effective dosage of any specific compound, the use of which is in the scope of present invention, will vary somewhat from compound to compound, patient to patient, and will depend upon the condition of the patient and the route of delivery. As a general proposition, a dosage from about 100 ng/kg to about 1 mg/kg will have therapeutic efficacy, with a dosage of from about 10 $\mu$g/kg to 100 $\mu$g/kg being preferred, with all weights being calculated based upon the weight of the active base, including the cases where a salt is employed. A dosage from about 10 $\mu$g/kg to about 10 mg/kg may be employed for topical administration, with a dosage from about 1 mg/kg to 10 mg/kg being preferred. Treatment can be administered once daily or several times per day for a period of 1 to 10 days or until the herpes viral infection is essentially controlled. Lower doses given less frequently can be used to prevent or reduce the incidence of recurrence of the infection.

Depending on the solubility of the particular formulation of active compound administered, the daily dose may be divided among one or several unit dose administrations. The dose may be a single unit dose, which may, for example, be administered several times a week or from 1 to 3 times a day. Treatments may continue week to week on a chronic basis as necessary (i.e., the active agent can be administered repeatedly). Administration of the active compounds may be carried out therapeutically or prophylactically, but preferably the compounds are administered therapeutically, either before symptoms of the herpes infection have appeared, or at a time when such symptoms are first appearing.

In accordance with the present method, an active compound as described herein may be prepared as a formulation suitable for topical (including buccal, sublingual, dermal and intraocular), oral, parenteral (including subcutaneous, intradermal, intramuscular, intravenous, and intraarticular), inhalation, rectal, and transdermal administration.

In the manufacture of a medicament according to the invention (a "formulation"), active agents or the pharmaceutically acceptable salts thereof (the "active compound") are typically admixed with, inter alia, an acceptable carrier. The carrier must, of course, be acceptable in the sense of being compatible with any other ingredients in the formulation and must not be deleterious to the subject. The carrier may be solid or liquid, or both, and is preferably formulated with the compound as a unit-dose formulation, for example, a tablet, which may contain from 0.05% to 99% by weight of the active compound. One or more active compounds may be incorporated in the formulations of the invention (e.g. the formulation may contain one or more additional antiviral agents as noted above), which formulations may be prepared by any of the well-known techniques if pharmacy consisting essentially of admixing the components, including one or more accessory therapeutic ingredients.

In addition to the active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 1 mg/mL. Compositions that are soluble in water in an amount from about 1 mg/mL to about 60 mg/mL are defined as "partially soluble." For certain applications, water soluble compounds or salts may be desirable, whereas for other applications water-insoluble compounds or salts likewise may be desirable.

Pharmaceutical compositions may be prepared from the water-insoluble active compounds, or salts thereof, such as aqueous base emulsions. In such an instance, the composition will contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds and salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the active compounds or salts thereof, may be lyophilized to produce a lyophilizate which may be reconstituted with a pharmaceutically acceptable carrier, such as water, to regenerate a liposomal suspension.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, e.g., *Pharmaceutical Research* 3, 318 (1986)) and typically take the form of an optionally buffered aqueous solution of the active compound.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for buccal (sublingual) administration include lozenges comprising the active compound in a flavored base, usually sucrose and acacia or tragacanth; and pastilles comprising the compound in an inert base such as gelatin and glycerin or sucrose and acacia.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Preferably, formulations for oral administration may include enteric coatings known in the art to prevent degradation of the formulation in the stomach and provide release of the drug in the small intestine. Also, the dosage of the formulation may be raised slightly to overcome any digestion of the active compound in the gastrointestinal (GI) tract. Alternatively, a "diverting compound" (e.g., a 3',5'-oligoadenylate compound) may be administered in conjunction with the active compound in order to provide competing substrates for such GI enzymes.

Formulations of the present invention suitable for parenteral administration comprise sterile aqueous and non-aqueous injection preparations of the active compound, which preparations are preferably isotonic with the blood of the intended recipient. These preparations may include antioxidants, buffers, bacteriostats, and solutes that render the formulation isotonic with the blood of the intended recipient. Aqueous and non-aqueous sterile suspensions may include suspending agents and thickening agents. The formulations may be presented in unit/dose or multi-dose containers, for example sealed ampules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid active compound, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble active compound of the present invention or a salt thereof, in a carrier which comprises water. A surfactant may be present which lowers the surface tension of the formulation sufficiently to result in the formation of droplets within the desired size range when subjected to nebulization.

The following examples are provided to illustrate the present invention, and should not be construed as limiting thereon. In these examples, M means molar, mM means millimolar, $\mu M$ means micromolar, nm means nanomolar, ml means milliliters, $\mu l$ means microliters, °C. means degrees Celsius, g means grams, and $\mu g$ means micrograms.

EXAMPLE 1

Clinical Testing of 2',5'-Oligoadenylates in Treatment of Oral and Genital Herpes Simplex The efficiency of Papirin A III, Papirin B III and Papirin C in treatment of oral and genital herpes was carried out on a clinical study group of 27 patients at the Gynecology and Obstetrics Clinic of Lumumba University (Moscow). Patients with oral herpes (with lesions visible on the lips, nostrils or ear flap) had, in general, suffered from irregular recurrency (an episode every two-six months) during the previous several years prior to the testing.

In the case of patients with oral herpes, visible herpes lesions were treated by the topical application of a dilute ($10^{-5}$–$3 \times 10^{-4}$M) aqueous solution of Papirin A III or B III. Application of the solutions was carried out by placing cotton wool or a gauze tampon pre-moistened with 30–100 $\mu L$ of the test solution over the lesion for 1–2 hours, two-four times a day.

Treatment of these patients with the Papirin solutions was started either on the first or second day after the initial appearance of itching and pain, accompanied usually by malaise and fever. After the application of the test solutions, the itching ceased and the overall status of patients had improved by the first to third day of treatment. In many cases, blisters either did not develop at all, or were converted rapidly into scabs. Complete recovery (disappearance of scab and swelling) took, on average, usually less than one week. No traces of skin erosion remained at the site of lesion after treatment. In all cases, relapses of the herpes after the treatment either became more seldom, or were not observed in the following 6–12 months.

Patients with genital herpes were treated according to the same procedure as with the oral herpes patients. In these patients, lesions were located on the genital lips, vulva, waist or buttocks. In these cases, patients in the study groups had experienced frequent disease recurrence in the past, with episodes lasting up to several weeks. In most cases in this study group, itching and pain disappeared two to four days after treatment had begun. In one case, in which the patients lesions had been aggravated by a large scratch wound, significant improvement was observed after 14 days of treatment. Only in one case (Papirin B III, #5) was recurrency was observed within two weeks after the end of treatment. In general, the repeated treatment of lesions resulted in slow, but complete recovery without relapse in the following months.

In both oral and genital herpes patients, treatment of the herpes lesion with either Papirin A III or Papirin B III led to a significant decrease in the duration of the acute period of the disease (by a magnitude of two-fold or more). The efficiency of treatment is only slightly dependent on the type of Papirine (A III better than B III) at concentrations between $1 \times 10^{-4}$M and $5 \times 10^{-4}$M. In no case was any adverse reaction (topical or systemic) or aggravation of the patient's state observed.

Tables 1 and 2 below provide the results of the clinical studies described above. Table 1 illustrates the effectiveness of Papirin A III against herpes infection. Table 2 illustrates the effectiveness of Papirin B III against herpes infection.

TABLE 1

Clinical testing of Papirin AIII for treatment of oral and genital herpes simplex

| Case | Location of lesion | Concentration, $10^{-4}$ M | Result (day after start of treatment) | | Conclusion[b] |
|------|--------------------|-----------------------------|--------------------|------------|----------------|
|      |                    |                             | visible changes[a] | disappearance |             |
| 1    | lips               | 1                           | 4                  | 7          | p              |
| 2    | lips               | 1                           | 2                  | 4          | p              |
| 3    | nostrils           | 1                           | 3                  | 6          | p              |

TABLE 1-continued

Clinical testing of Papirin AIII for treatment of oral and genital herpes simplex

| Case | Location of lesion | Concentration, $10^{-4}$ M | Result (day after start of treatment) visible changes[a] | disappearance | Conclusion[b] |
|---|---|---|---|---|---|
| 4  | lips | 1    | 2 | 4 | p |
| 5  | lips | 1    | 2 | 5 | p |
| 6  | lips | 3    | 2 | 4 | p |
| 7  | lips | 3    | 2 | 5 | p |
| 8  | lips | 3    | 2 | 4 | p |
| 9  | lips | 3    | 4 | 6 | p |
| 10 | lips | 3    | 2 | 3 | p |
| 11 | lips | 1[c] | 2 | 4 | p |

[a] Pain and fever ceasing, regress of blisters and appearance of scab
[b] p - positive, complete recovery (disappearance of scab and swelling, restoration of normal state of the skin) in less than one week of treatment. sp - semipositive, complete recovery takes more than one week of treatment.
[c] Papirin ATV

TABLE 2

Clinical testing of Papirin BIII for treatment of oral and genital herpes simplex

| Case | Location of lesion | Concentration, $10^{-4}$ M | Result (day after start of treatment) visible changes[a] | disappearance | Conclusion[b] |
|---|---|---|---|---|---|
| 1  | lips           | 5    | 2 | 4  | p  |
| 2  | vulva          | 1    | 5 | 9  | sp |
| 3  | lips           | 1    | 2 | 7  | p  |
| 4  | lips           | 3    | 2 | 3  | p  |
| 5  | genitals       | 3    | 1 | 4  | p  |
| 6  | genitals       | 3    | 4 | 8  | sp |
| 7  | lips           | 3    | 3 | 5  | p  |
| 8  | lips           | 3    | 2 | 3  | p  |
| 9  | lips, nostrils | 1    | 3 | 4  | p  |
| 10 | waist, buttocks| 3    | 2 | 5  | p  |
| 11 | chin           | 3    | 2 | 4  | p  |
| 12 | lips           | 3    | 2 | 10 | sp |
| 13 | lips, ear-flap | 5    | 3 | 10 | sp |
| 14 | lips           | 3[c] |   | 2  | p  |
| 15 | lips           | 2[c] | 2 | 4  | p  |
| 16 | genitals       | 3    | 2 | 4  | p  |

[a] Pain and fever ceasing, regress of blisters and appearance of scab
[b] p - positive, complete recovery (disappearance of scab and swelling, restoration of normal state of the skin) in less than one week of treatment. sp - semipositive, complete recovery takes more than one week of treatment.
[c] Papirin BIV.

The foregoing examples are illustrative of the present invention and are not to be construed as limiting thereof. The invention is defined by the following claims, with equivalents of the claims to be included therein.

That which is claimed is:

1. A method of treating a herpes infection in a subject in need of such treatment, comprising administering to said subject a compound of Formula I:

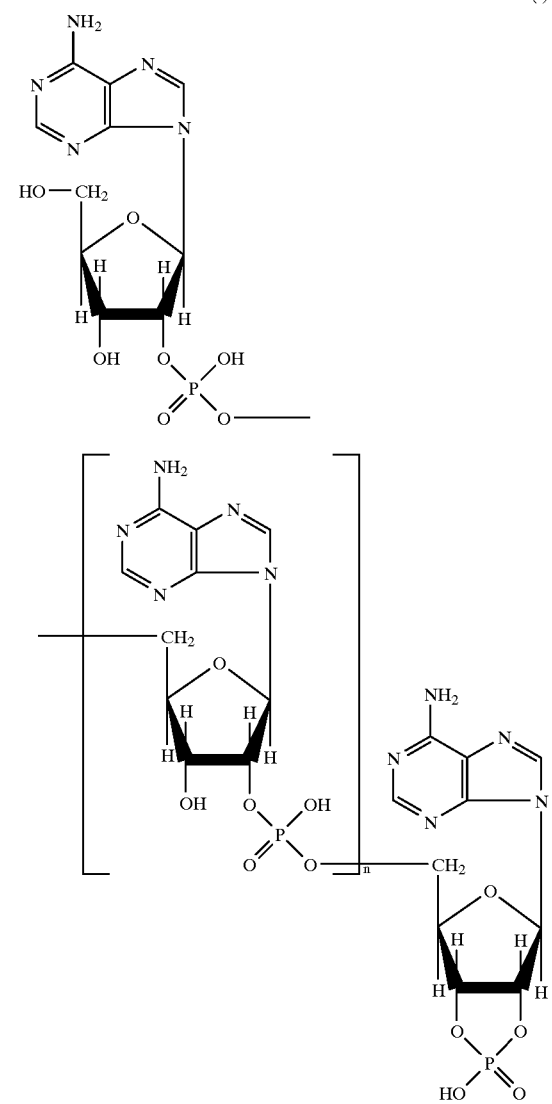

(I)

wherein n is 0, 1, 2, or 3;
or a pharmaceutically acceptable salt thereof, in an amount effective to treat the herpes infection.

2. The method according to claim 1, wherein said subject is afflicted with genital herpes.

3. The method according to claim 1, wherein said subject is afflicted with oral herpes.

4. The method according to claim 1, wherein said subject has a latent herpes infection and said compound is administered in a therapeutically effective amount.

5. A method according to claim 1, wherein said compound of Formula I is administered topically.

6. A method according to claim 1, wherein said compound of Formula I is administered orally.

* * * * *